US00PP28736P2

(12) United States Plant Patent
Van Swieten

(10) Patent No.: US PP28,736 P2
(45) Date of Patent: Dec. 5, 2017

(54) ***PHALAENOPSIS* ORCHID PLANT NAMED 'PHALOFMO'**

(50) Latin Name: ***Phalaenopsis* hybrid**
Varietal Denomination: PHALOFMO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/330,509

(22) Filed: Sep. 29, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALOFMO', particularly characterized by having light purple flowers, 1 to 2 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALOFMO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALOFMO'.

The new *Phalaenopsis* plant is a product of a planned breeding program conducted by the inventor in Bleiswijk, The Netherlands. The objective of this breeding program was to create a new *Phalaenopsis* plant with light purple flowers suitable for potted plant production.

The new *Phalaenopsis* plant 'PHALOFMO' is a result of cross-pollination made by the inventor in August 2006 in Bleiswijk, The Netherlands of the proprietary female, or seed parent, *Phalaenopsis* hybrid 'PHALCOBYL' (unpatented) with the proprietary male, or pollen parent, *Phalaenopsis* hybrid 'PHALMACHE' (unpatented).

The new *Phalaenopsis* was selected by the inventor as a single plant within the progeny of the stated cross-pollination in a controlled greenhouse in Bleiswijk, The Netherlands in August 2009. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALOFMO' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALOFMO' as a new and distinct variety of *Phalaenopsis* plant.

1) Light purple flowers;
2) 1 to 2 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in July 2016. Colors in the photographs may differ from the color values cited in the detailed botanical description, which accurately describe the actual colors of the new variety.

DESCRIPTION OF THE NEW VARIETY

Figure 1:
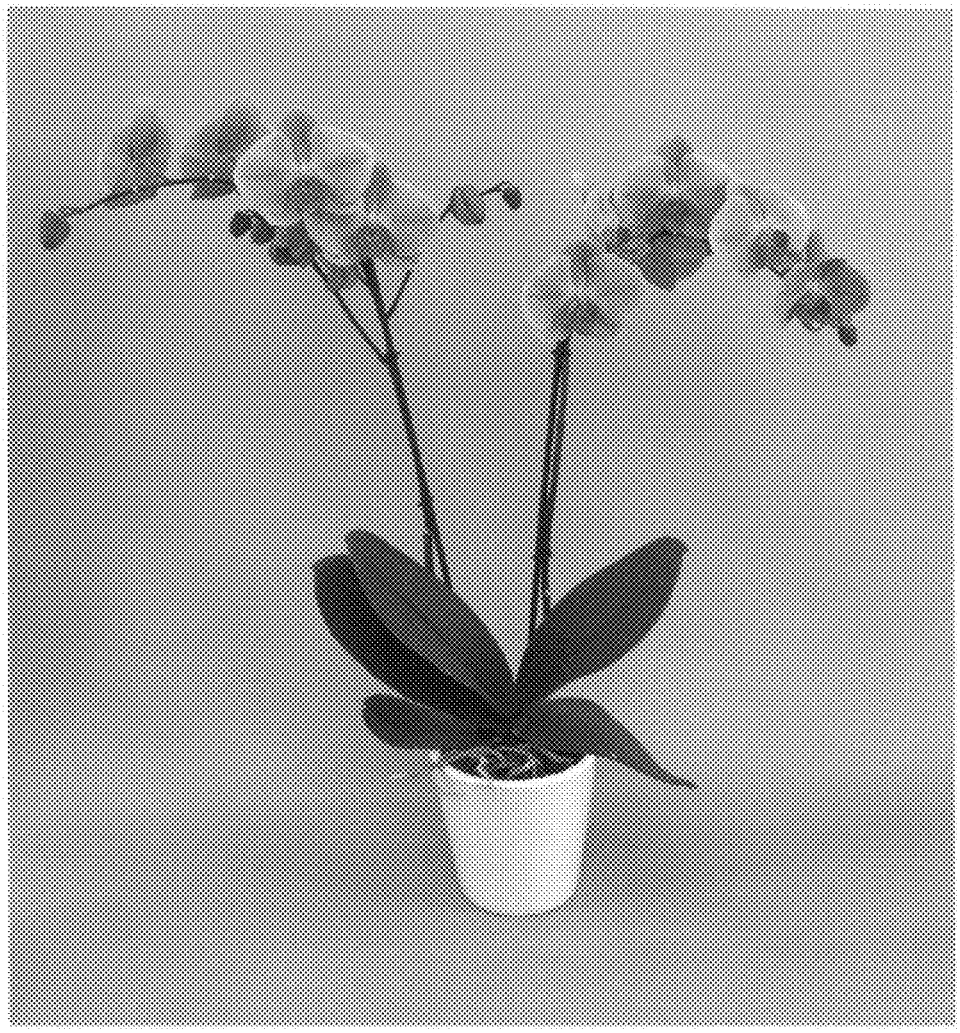
FIG. 1 shows the overall plant habit, including blooms, buds and foliage of 'PHALOFMO'.
Figure 2:
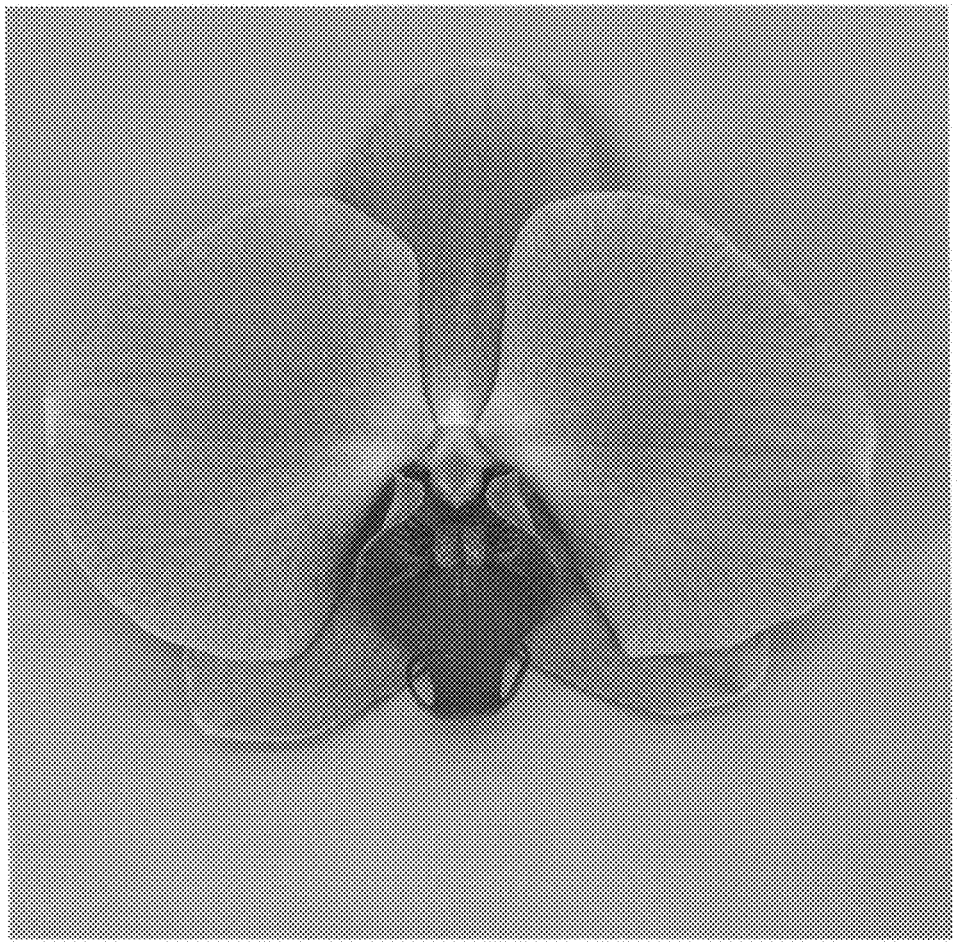
FIG. 2 shows a close-up of a flower of 'PHALOFMO'.
Figure 3:
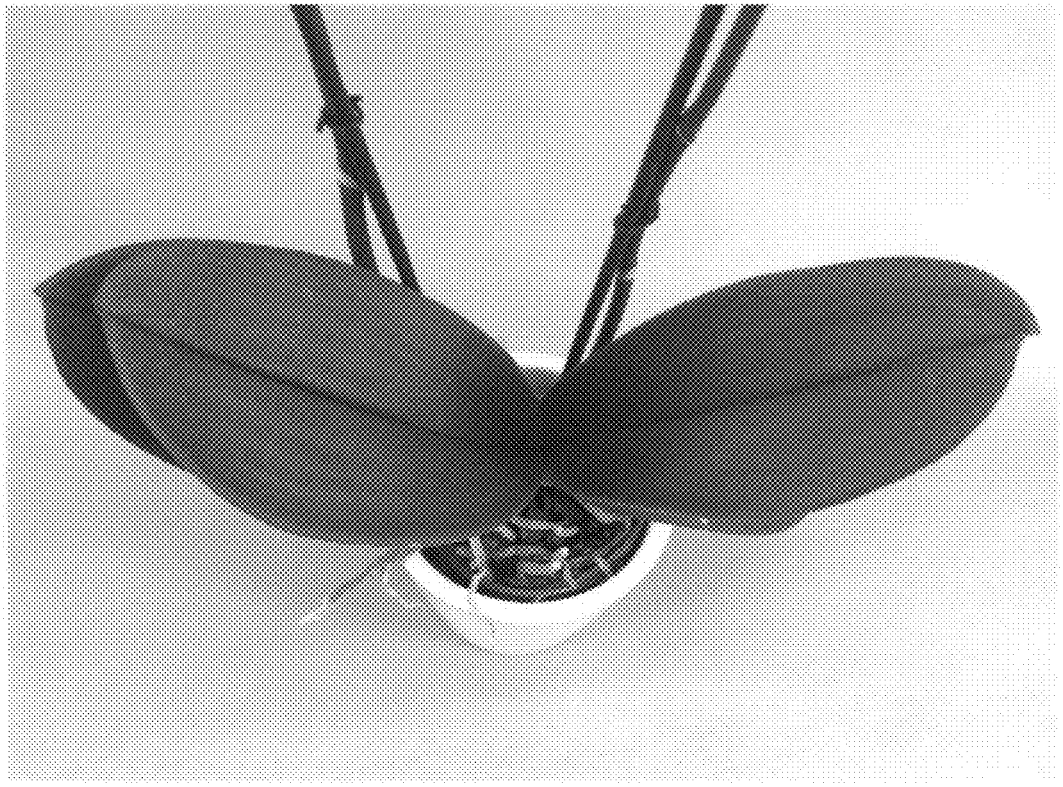
FIG. 3 shows a close-up of the leaves of 'PHALOFMO'.

The following detailed description sets forth the distinctive characteristics of 'PHALOFMO'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in July 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALOFMO'.

Parentage:

*Female parent*.—*Phalaenopsis* cultivar 'PHALCOBYL' (unpatented).

*Male parent*.—*Phalaenopsis* cultivar 'PHALMACHE' (unpatented).

Propagation:

*Type*.—Meristem tissue culture.

Roots:

*Root description*.—Greyed-green colored roots with branching lateral roots having light purple colored root tips.

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 51.0 cm to 61.0 cm.

*Width* (*measured from leaf tips*).—About 36.0 cm to 40.0 cm.

*Vigor*.—Strong.

Leaves:

*Mature leaves*.—Quantity per plant: 6 to 7 leaves are produced before flowering. Length (fully expanded): 19.0 cm to 21.0 cm. Width: 9.0 cm to 10.0 cm. Shape: Oblong. Base shape: Moderately elongated. Apex: Unequal obtuse. Leaf blade angle with the petiole (measured from the horizontal position): Between 30 degrees and 60 degrees. Leaf margin: Entire. Leaf variegation: Present (lightly mottled). Color: Upper surface: RHS 147A. Lower surface: RHS 147B. Texture: Rough. Thickness: 2.3 mm to 2.6 mm. Venation: Pattern: Parallel. Color of the midvein: Upper surface: RHS 147A. Lower surface: RHS 147B.

Peduncle:

*Quantity per plant*.—1 to 2.

*Number of flowers per peduncle*.—11 to 16.

*Length*.—51.0 cm to 61.0 cm.

*Diameter*.—6.0 mm to 6.3 mm.

*Strength*.—Strong.

*Aspect*.—Upright to slightly pendant.

*Texture*.—Slightly rough.

*Color*.—Brown (RHS 200A).

*Internode length*.—3.5 cm to 4.0 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 250.0 mm to 280.0 mm.

*Flowering time*.—First flowers can be expected 10 to 11 months after planting in a 12 cm (diameter) pot.

*Flower*.—Height: 86.0 mm to 91.0 mm. Diameter: 100.0 mm to 105.0 mm. Depth of lip: 25.0 mm to 27.0 mm.

*Flower longevity*.—On the plant: 8 to 12 weeks.

*Fragrance*.—Absent.

*Flower bud*.—Average size: Medium. Length: 19.0 mm to 21.0 mm. Width: 17.0 mm to 19.0 mm. Shape: Egg shaped. Color: Dark purple (RHS 187C).

*Petals*.—Arrangement: Open/free. Shape: Semi-circular. Apex: Rounded and asymmetric. Margin: Slightly undulated. Length (from base to tip): 48.0 mm to 50.0 mm. Width: 58.0 mm to 60.0 mm. Color (when fully opened): Upper surface: Basic color: Light purple (RHS N78D). Over color: Lighter purple (RHS 76C and 76D) at the center and edge. Lower surface: Basic color: Light purple (RHS N78D). Over color: Purple (RHS N78B) at the base and lighter purple (RHS 76D) at the edge.

*Dorsal sepal*.—Shape: Broad elliptic. Apex: Rounded to slightly emarginated and symmetric. Margin: Entire. Length (from base to tip): 48.0 mm to 50.0 mm. Width: 35.0 mm to 37.0 mm. Color (when fully opened): Upper surface: Basic color: Purple (RHS N78C). Over color: Light purple (RHS 76C). Lower surface: Basic color: Purple (RHS N78B). Over color: Light purple (RHS N78D).

*Lateral sepals*.—Shape: Ovate. Apex: Obtuse and asymmetric. Margin: Entire. Length (from base to tip): 50.0 mm to 52.0 mm. Width: 29.0 mm to 31.0 mm. Color (when fully opened): Upper surface: Basic color: Purple (N78D). Over color: Light purple (RHS 76B). Lower surface: Basic color: Purple (RHS 78B). Over color: Purple (RHS 78C).

*Labellum* (*lip*).—Whiskers: Present. Length of whiskers: 14.0 mm to 16.0 mm. Color of whiskers: Purple (RHS N78A). Pubescence on the lip: Absent.

*Lateral lobe*.—Shape: Spatulate. Margin: Entire. Length (from base to tip): 22.0 mm to 24.0 mm. Width: 15.0 mm to 17.0 mm. Color: White (RHS NN155C) at the base; red-brown (RHS 181A) on one side. and light purple (RHS N78D) towards the edge with purple stripes (RHS N78A).

*Apical lobe*.—Shape: Triangular. Margin: Entire. Length: 22.0 mm to 24.0 mm. Width: 24.0 mm to 26.0 mm. Color: Yellow (RHS 14C) and red-brown (RHS 181A) at the base; purple (RHS N78A and NN78A) towards the edge.

*Callus*.—Height: 0.6 cm to 0.8 cm. Length: 0.7 cm to 0.9 cm. Width: 0.5 cm to 0.7 cm. Color: Yellow (RHS 13A) and dotted (RHS 172A).

*Reproductive organs*.—Column: Length: 10.0 mm to 12.0 mm. Diameter: 5.8 mm to 6.0 mm. Color: Purple (RHS N78B and 76B). Pollinia: Quantity: 2. Diameter: 1.1 mm to 1.3 mm. Color: Yellow-orange (RHS 23A). Ovary: Length: 10.0 mm to 12.0 mm. Diameter: 2.3 mm to 2.5 mm. Pedicel: Length: 41.0 mm to 43.0 mm. Diameter: 3.0 mm to 3.2 mm. Color: Diluted purple-red (RHS N77B) at the base; light green (RHS 193B) and light purple (RHS 75B) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

'PHALOFMO' differs from female parent plant 'PHALCOBYL' (unpatented) in that 'PHALOFMO' has a pattern on the edge of the lateral lobe and purple whiskers, whereas 'PHALCOBYL' does not have a pattern on the edge of the lateral lobe and has light purple whiskers. Additionally, 'PHALOFMO' has shorter whiskers, wider petals and a wider apical lobe than 'PHALCOBYL'.

'PHALOFMO' differs from male parent plant 'PHALMACHE' (unpatented) in that 'PHALOFMO' has purple whiskers, a rounded petal apex and a pattern on the edge of the lateral lobe, whereas 'PHALMACHE' has red-purple whiskers, a mucronate petal apex and does not have a pattern on the edge of the lateral lobe. Additionally, 'PHALOFMO' has shorter whiskers, a wider apical lobe and thinner petals than 'PHALMACHE'.

'PHALOFMO' is most similar to the commercial *Phalaenopsis* plants named 'PHALBAZOKU' (unpatented) and 'PHALCIMEI' (U.S. Plant patent application Ser. No. 14/544,672). 'PHALOFMO' differs from the commercial variety 'PHALBAZOKU' in that 'PHALOFMO' has an open/free petal arrangement and light purple flowers, whereas 'PHALBAZOKU' has a touching or overlapping petal arrangement and purple flowers. Additionally, 'PHALOFMO' has slightly larger flowers and thinner petals than 'PHALBAZOKU'.

'PHALOFMO' differs from the commercial variety 'PHALCIMEI' in that 'PHALOFMO' has purple whiskers and light purple flowers, whereas 'PHALCIMEI' has red and yellow whiskers and purple flowers. Additionally, 'PHALOFMO' has shorter whiskers, a wider apical lobe, thinner petals and smaller flowers than 'PHALCIMEI'.

I claim:

1. A new and distinct variety of *Phalaenopsis* plant named 'PHALOFMO', substantially as described and illustrated herein.

* * * * *